United States Patent [19]

Boeck et al.

[11] Patent Number: 5,286,631
[45] Date of Patent: Feb. 15, 1994

[54] PROCESS FOR PRODUCING THE A10255 COMPLEX AND CORRESPONDING MICROORGANISM

[75] Inventors: LaVerne D. Boeck, Indianapolis; Otis W. Godfrey, Jr., Greenwood; Karl H. Michel, Indianapolis, all of Ind.

[73] Assignee: Eli Lilly and Company, Indianapolis, Ind.

[21] Appl. No.: 663,194

[22] Filed: Feb. 28, 1991

Related U.S. Application Data

[63] Continuation of Ser. No. 941,473, Dec. 15, 1986, abandoned.

[51] Int. Cl.$^5$ .................. C12P 21/04; C12N 1/20
[52] U.S. Cl. ...................... 435/71.3; 435/253.5; 435/252.1; 435/886; 435/170; 435/822
[58] Field of Search ............. 435/822, 71.3, 170, 435/252.1, 253.8, 886

[56] References Cited

U.S. PATENT DOCUMENTS

| | | | |
|---|---|---|---|
| 3,650,904 | 3/1972 | Hata | 935/129 |
| 3,689,639 | 9/1972 | Bergy et al. | 424/117 |

FOREIGN PATENT DOCUMENTS

| | | | |
|---|---|---|---|
| 0112233 | 12/1983 | European Pat. Off. | A23K 1/17 |
| 0274873 | 7/1988 | European Pat. Off. | C07K 11/00 |

OTHER PUBLICATIONS

J. M. Liesch and K. L. Rinehart, "Berninamycin 3. Total Structure of Berninamycin A", *J. Amer. Chem. Soc.* 99 (5), 1645–1646 (1977).
ATCC Catalogue of Bacteria, 1985, p. 184.
Gardner et al., *Br. J. Exp. Pathol.* 23, 123 (1942).
*Index of Antibiotics from Actinomyces*, H. Umezawa, Ed., University of Tokyo Press, vol. I, p. 533 (1967).
*Chem. Abstr.* 79 (25): 144 870n (1973), abstracting JP–B–7300,075 (Kyowa Fermentation Industry).
*Chem. Abstr.* 68 (25): 112 328y (1968), abstracting M. A. Laneelle et al., *Ann Inst. Pasteur* 114 (3), 305–312 (1968).
*Bergey's Manual of Determinative Bacteriology*, 9th Ed., 194, pp. 748–750.
*CRC Handbook of Microbiology*, vol. III, 1973, p. 825.
R. Suhadolnik in Vanek et al., *Genetics of Industrial Microorganisms*, vol. II, 1973, pp. 335–338.
ATCC Catalog of Bacteria, 1989, p. 236.

*Primary Examiner*—Irene Marx
*Attorney, Agent, or Firm*—Steven A. Fontana; Leroy Whitaker

[57] ABSTRACT

Newly-discovered antibiotic A10255 factors B, C, E, and F are produced by submerged aerobic fermentation of previously-unknown *Streptomyces gardneri* strain NRRL 15922, or an A10255-producing variant, mutant or recombinant thereof. The antibiotics are active against a wide variety of pathogenic bacteria, and also enhance feed-utilization efficiency in chickens, weanling pigs and cattle.

8 Claims, No Drawings

PROCESS FOR PRODUCING THE A10255 COMPLEX AND CORRESPONDING MICROORGANISM

This application is a continuation of application Ser. No. 06/941,473, filed on Dec. 15, 1986, now abandoned.

SUMMARY OF THE INVENTION

This invention relates to a new and improved method of producing the A10255 complex and its individual factors, and the novel microorganism that produces the complex. This method involves fermenting *Streptomyces gardneri*, NRRL 15922 under submerged aerobic conditions until a substantial amount of the A10255 complex is produced. A further step in the process is the isolation of the complex from the fermentation broth, and especially from the mycelia. The A-10255 factors B, C, E, and F are isolated from the complex by chromatographic means.

This invention further relates to the biologically pure culture of *Streptomyces gardneri* strain NRRL 15922, which is useful for the production of the A10255 antibiotic complex (and its constituent individual factors) and the A10255-producing variant, mutants or recombinant thereof.

DETAILED DESCRIPTION

This invention relates to a process for cultivating the A10255 complex, which comprises cultivating *Streptomyces gardneri* NRRl 15922, or an A10255-producing variant, mutant or recombinant thereof, in a culture medium containing assimilable sources of carbon, nitrogen, and inorganic salts under submerged aerobic fermentation conditions until the A10255 antibiotic complex is produced. A preferred process includes the additional step of separating the A10255 complex from the culture medium. Further preferred processes include the additional step of isolating antibiotic A10255 factor B, C, E, or F from the separated A10255 complex.

A further aspect of the invention is a biologically pure culture of the microorganism *Streptomyces gardneri* NRRL 15922, or an A10255-producing mutant, variant or recombinant thereof. A preferred embodiment of this aspect of the invention is the biologically pure culture of the microorganism *Streptomyces gardneri* NRRL 15922.

As is the case with many antibiotic-producing cultures, fermentation of an A10255-producing strain of *S. gardneri* NRRL 15922 results in the coproduction of a number of antibiotic substances. Antibiotic A10255 factor B is the major factor produced by this culture, and factors C, E, and F are produced in minor yet isolable amounts. Other factors are present in only minor quantities or are relatively unstable. The amounts of the individual factors coproduced may vary somewhat from fermentation to fermentation.

The antibiotic factors B, C, E, and F, coproduced during the fermentation and obtained as a mixture, are termed the A10255 complex. The amounts of the individual factors are separated from each other and isolated as distinct entities with the following physical and biological properties.

The antibiotic A10255 complex and its individual factors and method for producing them are claimed in U.S. patent application No. 06/941,894, of Karl H. Michel, LaVerne D. Boeck, Herbert A. Kirst, Marvin M. Hoehn, and Eugene T. Seno.

Physical Characteristics of the Compounds

A10255 Factor B

A10255 Factor B is a non-crystalline white to light-yellow powder which is soluble in dimethylsulfoxide, dimethylformamide, pyridine, chloroform/methanol mixtures, and 4:1 (v:v) tetrahydrofuran:water.

Elemental analysis of factor B indicates the following approximate percentage composition (average): carbon, 49.25%; hydrogen, 3.94%; nitrogen, 15.65%; oxygen, 21.36%; and sulfur, 6.73%.

The apparent molecular weight of A10255 factor B was determined by fast atom bombardment mass spectrometry to be approximately 1244 daltons.

Electrometric titration of A10255 factor B measured in 66% aqueous dimethylformamide indicates the presence of three titratable groups with pKa values of 4.9, 11.2 and 12.8. Amino acid analysis of factor B (after hydrolysis with 6N hydrochloric acid) indicates the presence of ammonia (5,268 nanomoles/mg) and threonine (629 nanomoles/mg). The analysis also evinced a large, unidentified peak coming before the position for the histidine peak.

The ultraviolet absorption spectrum for factor B obtained in neutral, acidic, and basic methanol demonstrated $\lambda_{max}$ of 245 nm ($\epsilon = 66,000$). The infrared absorption spectrum of Factor B in a potassium bromide disc exhibit as the more significant absorption maxima at 3373, 2969, 2932, 2875, 1661, 1598, 1520, 1494, 1395, 1250, 1114, 1084, 996, 932, and 900 $cm^{-1}$. The proton nuclear magnetic resonance spectrum of factor B was obtained in perdeuterated dimethylsulfoxide at 270 MHz and had the following absorption maxima: δ 6 10.56, 9.98, 9.94, 9.82, 9.62, 9.60, 9.43, 8.90, 8.85, 8.69, 8.52, 8.48, 8.40, 8.26, 8.24, 8.09, 6.88, 6.53, 6.51, 6.40, 5.97, 5.83, 5.80, 5.65, 5.55, 5.45, 5.10, 4.80, 4.68, 4.63, 4.24, 2.70, 2.20, 2.19, 1.82, 1.36, 1.12, and 1.00.

A10255 Factor C

A10255 factor C is a non-crystalline white to light-yellow powder which is soluble in dimethylsulfoxide, dimethylformamide, pyridine, 1:1 (v:v) methylene chloride/methanol, and 4:1 (v:v) tetrahydrofuran:water.

Elemental analysis of factor C indicates the following approximate percentage composition (average): carbon, 49.18%; hydrogen, 3.86%; nitrogen, 17.89%; oxygen, 18.28%; and sulfur, 6.46%.

The apparent molecular weight of A10255 factor C was determined by fast atom bombardment mass spectrometry to be approximately 1174 daltons.

Electrometric titration of A10255 factor C measured in 66% aqueous dimethylformamide (initial pH, 7.29) indicated the presence of two titratable groups with pKa values of 2.9 (uncertain) and 12.0. Amino acid analysis of the factor C (after hydrolysis with 6N hydrochloric acid) indicated the presence of ammonia (7,429 nanomoles/mg) and threonine (758 nanomoles/mg). The analysis also evinced a large, unidentified peak coming before the position for the histidine peak.

The ultraviolet absorption spectrum for factor C obtained in neutral, acidic, and basic methanol demonstrated $\lambda_{max}$ of 245 nm ($\epsilon = 63,000$). The infrared absorption spectrum in a potassium bromide disc exhibits more significant absorption maxima at 3375, 2973, 2932, 2876, 1661, 1597, 1494, 1427, 1345, 1305, 1249, 1111, 1083, 984, 933, and 894 $cm^{-1}$. The proton nuclear magnetic resonance spectrum of factor C was obtained in perdeuterated dimethylsulfoxide at 360 MHz and had the following absorption maxima: δ 10.51, 10.08, 9.84, 9.57, 9.10, 8.88, 8.03, 7.94, 7.53, 5.15 (all of the foregoing maxima are exchangeable with D$_2$O), 8.67, 8.59, 8.51, 8.49, 8.38, 8.25, 8.24, 6.57, 6.52, 6.38, 6.11, 5.91, 5.78, 5.74, 5.70, 5.65, 5.63, 5.44, 5.15, 4.79, 4.67, 4.63, 4.23, 2.21, 1.62, 1.11, and 1.01.

A10255 Factor E

A10255 factor E is a non-crystalline white to light-yellow powder which is soluble in dimethylsulfoxide, dimethylformamide, pyridine, chloroform/methanol mixtures, and 4:1 (v:v) tetrahydrofuran:water.

Elemental analysis of factor E indicates the following approximate percentage composition (average): carbon, 48.03%; hydrogen, 3.91%; nitrogen, 15.76%; oxygen, 17.09%; and sulfur, 5.63%.

The apparent molecular weight of A10255 factor E was determined by fast atom bombardment mass spectrometry to be approximately 1258 daltons.

Electrometric titration of A10255 factor E measured in 66% aqueous dimethylformamide indicates the presence of three titratable groups with pKa values of 4.85, 11.1, and 13.2. Amino acid analysis of the factor E (after hydrolysis with 6N hydrochloric acid) indicates the presence of ammonia (8,580 nanomoles/mg) and threonine (716 nanomoles/mg). The analysis also evinced a large, unidentified peak coming before the position of the histidine peak.

The ultraviolet absorption spectrum for factor E obtained in neutral, acidic, and basic methanol demonstrated a $\lambda_{max}$ of 245 nm ($\epsilon$ = 77,000). The infrared absorption spectrum of Factor C in a potassium bromide disc exhibits more significant absorption maxima at 3367, 3361, 2966, 1664, 1501, 1389, 1254, 1102, and 889 cm$^{-1}$. The proton nuclear magnetic resonance spectrum of factor B was obtained in perdeuterated dimethylsulfoxide at 270 MHz and had the following adsorption maxima: δ 10.54, 10.00, 9.94, 9.81, 9.60, 9.56, 9.45, 8.89, 8.84, 8.66, 8.59, 8.50, 8.47, 8.39, 8.25, 8.22, 8.10, 6.53, 6.50, 6.24, 5.95, 5.86, 5.84, 5.77, 5.64, 5.55, 5.52, 5.44, 5.10, 4.80, 4.66, 4.64, 4.22, 2.78, 1.60, 1.11, and 1.00.

A10255 Factor F

A10255 factor F is a white to light-yellow non-crystalline powder which is soluble in dimethylsulfoxide, dimethylformamide, pyridine, 1:1 (v:v) methyl chloride/methanol, and 4:1 (v:v) tetrahydrofuran:water.

Elemental analysis of factor F indicates the following approximate percentage composition (average): carbon, 49.65%; hydrogen, 4.23%; nitrogen, 17.11%; oxygen, 22.08%; and sulfur, 7.78%.

The apparent molecular weight of A10255 factor F was determined by field desorption mass spectrometry to be approximately 1188 daltons.

Electrometric titration of A10255 factor F measured in 66% aqueous dimethylformamide (starting pH of 7.08) indicates the presence of a titratable group with a pKa value of 12.5. Amino acid analysis of the factor F (after hydrolysis with 6N hydrochloric acid) indicates the presence of ammonia (7,226 nanomoles/mg) and threonine (735 nanomoles/mg). The analysis also evinced a large, unidentified peak coming before the position of the histidine peak.

The ultraviolet absorption spectrum for factor F obtained in neutral, acidic, and basic methanol demonstrated a $\lambda_{max}$ of 245 nm ($\epsilon$ = 71,500). The infrared absorption spectrum in a potassium bromide disc exhibits more significant absorption maxima at 3369, 2943, 2907, 2846, 1663, 1588, 1519, 1493, 1425, 1337, 1288, 1251, 1151, 1110, 1083, 995, 927, 890, 807, 776, and 751 cm$^{-1}$. The proton nuclear magnetic resonance spectrum of factor F was obtained in perdeuterated dimethylsulfoxide at 10 360 MHz and had the following adsorption maxima: δ 10.51, 10.17, 9.88, 9.77, 9.54, 9.10, 8.90, 8.88, 8.66, 8.59, 8.51, 8.49, 8.38, 8.25, 8.24, 8.06, 7.94, 7.53, 6.56, 6.51, 6.27, 6.23, 6.12, 6.12, 5.96, 5.77, 5.76, 5.71, 5.71, 5.64, 5.62, 5.47, 5.14, 4.77, 4.65, 4.62, 4.20, 2.77, 2.48, 2.48, 1.58, 1.08, 0.98, and 0.98.

Taxonomy of the A10255.2 Strain

The A10255.2 strain, (referred to above as the Streptomyces gardneri strain NRRL 15922) is an NTG mutant of the A10255.1 strain. The latter strain is the subject of U.S. patent application No. 06/941,894, Karl H. Michel, LaVerne D. Boeck, Herbert A. Kirst, Marvin M. Hoehn, and Eugene T. Seno, and is referred to therein as a strain of *Streptomyces gardneri* NRRL 15537.

As there are many similarities in the taxonomies of the A10255.1 and A10255.2 strains, the taxonomy of the A10255.1 strain will be discussed first. The taxonomic differences between the A10255.1 and .2 strains will then be set forth in tabular form.

Taxonomy of the A10255.1 Strain

Taxonomic studies of the A10255.1 strain were carried out by Frederick P. Mertz of the Lilly Research Laboratories. Based on these studies, the organism is classified as a new strain of *Streptomyces gardneri* (Waksman 1942) Waksman 1961 ATCC 23911. This classification is based on an examination of published descriptions of this species [R. E. Buchanan, and N. E. Gibbons (eds.), "Bergey's Manual of Determinative Bacteriology", 8th Edition, The Williams and Wilkins Co., Baltimore, 1974; E. B. Shirling and D. Gottlieb, "Cooperative Description of Type Cultures of Streptomyces", *Int. J. Syst. Bacteriol.* 18(4):279–392 (1968); and S. A. Waksman, "The Actinomycetes Vol. II", The Williams and Wilkins Co., Baltimore, 1961]and simultaneous laboratory comparsions.

Methods Used

The methods recommended by the International Streptomyces Project (ISP) for the characterization of Streptomyces species [E. B. Shirling and D. Gottlieb, "Methods for Characterization of Streptomyces Species", *Int. J. Syst. Bacteriol.* 16(3), 313–340 (1966)]have been followed along with certain supplementary tests [D. J. Blazevic and G. M. Ederer, "Principles of Biochemical Tests in Diagnostic Microbiology", John Wiley and Sons, Inc., New York, 1975].

Carbon utilization was determined on ISP No. 9 basal medium to which filter-sterilized carbon sources were added to equal a final concentration of 1.0 percent. Plates were incubated at 30° C. and read after 14 days.

Melanoid pigment production (chromogenicity) was determined with ISP No. 1 (tryptone-yeast extract broth), ISP No. 6 (peptone-yeast extract iron agar), ISP No. 7 (tyrosine agar), and modified ISP No. 7 which has tyrosine removed.

Starch hydrolysis was determined by testing for the presence of starch with iodine on ISP No. 4 (inorganic salts-starch agar) plates (see Blazevic and Ederer, supra). .

Morphology was studied using an optical light microscope. A scanning electron microscope (SEM) was used to study the spore surface ornamentation.

Sodium chloride tolerance was measured by adding sodium chloride to ISP No. 2 agar to equal the concentration desired.

ICSS-NBS Centroid Color Charts, standard sample No. 2106 (National Bureau of Standards, 1958, U.S. Department of Commerce, Washington, D.C.) and the Color Harmony Manual (4th ed., Color Standards Department, Container Corporation of America, Chicago, Ill., 1958) were used to assign color names.

The cell wall sugars were determined with the procedure of M. P. Lechevalier, "Identification of Aerobic Actinomycetes of Clinical Importance," *J. Lab. Clin. Med.*, 71, 934–944 (1968). The isomers of diaminopimelic acid (DAP) were established by the chromatographic methods set forth in B. Becker, M. P. Lechevalier, R. E. Gordon, and H. A. Lechevalier, "Rapid Differentiation between Nocardia and Streptomyces by Paper Chromatography of Whole-cell Hydrolysates", *Appl. Microbiol* 11, 421–423 (1964).

Cultural Characteristics

A10255.1 is characterized by limited vegetative and very poorly developed aerial mycelia. The aerial mycelia have a spore mass color in the white (W) to gray (GY) color series. The nearest matching color tab in the Tresner and Backus system [Color Harmony Manual, supra, and E. J. Backus and H. D. Tresner, "System of Color Wheels for Streptomyces Taxonomy, *Appl. Microbiol.*, 11, 335–338 (1956)]for the white color series is b oyster white and in the gray color series is d light gray. This cultural feature is best observed on glycerol asparagine agar (ISP No. 5). Aerial mycelia are so poorly developed on most media that a color determination is very difficult.

The reverse side of this culture has no distinctive pigments. The color of the reverse side is orange-yellow to yellow-brown and the color is unaffected by pH. The only soluble pigment produced is a light brown pigment on tyrosine agar ISP No. 7 and tomato paste oatmeal agar (TPO) and a light-orange pigment on Glycerol-Glycine agar. When plated for variability, this culture was stable and homogeneous.

Cultural characteristics of the A10255.1 strain and *S. gardneri* strain ATCC 23911 are set forth below in Table 1.

TABLE 1

| | Cultural Characteristics of A10255.1 and *S. gardneri* | |
|---|---|---|
| Agar | A10255.1 | *S. gardneri* |
| ISP No. 2 | $^a$G: Fair | Fair |
| | $^b$R: 72.d.OY | 72.d.OY |
| | $^c$Am: Poor: b White (edges only) d light Gray | Poor: d light Gray (edges only) |
| | Sp: None | None |
| ISP No. 3 | G: Trace to Fair | Trace |
| | R: 70.1.OY | — |
| | Am: Trace: b White (edges only) | None — |
| | Sp: None | None |
| Calcium Malate | G: Fair | Fair |
| | R: 79.1.gy.yBr | 93.yGray |
| | Am: None → trace | Trace: b White (edges only) |
| | SP: None | None |
| Czapek's | G: Fair | Abundant |
| | R: 93.yGray | 79.1.gy.yBr |
| | Am: Poor: b White | Abundant: b White |
| | Sp: None | None |
| Glucose Asparagine | G: Fair | Fair |
| | R: 72.d.OY | 90.gy.Y |
| | Am: Poor: b White | None: — |
| | Sp: None | None |
| ISP No. 7 | G: Good | Good |
| | R: 54.brO | 77.m.yBr |
| | Am: Poor: b White | Poor: b White |
| | Sp: light-brown | very light brown |
| Glycerol Glycine | G: Fair | Fair - (wrinkled surface) |
| | R: 53.m.O (no pH change) | 90. gy.Y |
| | Am: None | None |
| | Sp: light-orange | None |
| TPO | G: Good | Good |
| | R: 54. brO (no pH change) | 72.d.OY |
| | Am: Poor: (edges only) 3ca pale orange yellow | Poor: (edges only) d light Gray |
| | Sp: light orange-brown | None |
| ISP No. 4 | G: Fair | Fair |
| | R: 71.m.OY | 91.d.gy.Y |
| | Am: Poor: b White | Poor: d light Gray |
| | Sp: None | None |
| ISP No. 5 | G: Fair | Fair |
| | R: 70.1.OY | 90.gy.Y |
| | Am: Fair: b White to d l.Gray | Trace: — |

TABLE 1-continued

| | Cultural Characteristics of A10255.1 and *S. gardneri* | |
|---|---|---|
| Agar | A10255.1 | *S. gardneri* |
| | Sp: None | None |

<sup>a</sup>G = Growth; R = Reverse; Am = Aerial Mycelia; Sp = Soluble pigment.
<sup>b</sup>Coding of reverse colors follows the ICSS-NBS System, Supra.
<sup>c</sup>Coding of aerial color follows the Color Harmony Manual, Supra.

Morphological Characteristics

Culture A10255.1 produces a poorly developed non-fragmenting aerial mycelium which is monopodially branched. Sporophores are arranged as straight and flexuous branches. No spirals, sclerotia, sporangia, or motile spores were observed. A10255.1 is placed in the Rectus-flexibilus (RF) section of Pridham et al. [T. G. Pridham et al., "A Guide for the Classification of Streptomyces According to Selected Groups", *Appl. Microbiol.*, 6, 52–79 (1957)].

The same morphology is observed on all media where aerial mycelia could be observed. Mature spore chains generally contain from 10 to 50 spores per chain.

The spore shape is cylindrical. The spore size ranges from 0.9–1.0 μM in length and 0.5–0.6 μM in width. The average size is 1.6×0.6 μM. The spore surface ornamentation is smooth.

Physiological Characteristics

Whole cell hydrolysates contain LL-diaminopimelic acid with no meso isomer present. Sugars present in whole cell hydrolysates were glucose, mannose, and ribose. These characteristics represent a Type I cell wall and a NC, or no characteristic, sugar pattern [M. P. Lechevalier, supra]. This combination of major cell wall constituents is indicative of the genus Streptomyces [M. P. Lechevalier, supra, and R. E. Buchanan and N. E. Gibbons (eds)., supra].

The carbon utilization pattern for A10255.1 is as follows: L-arabinose, D-fructose, D-galactose, D-glucose, i-inositol, raffinose, and D-xylose are utilized for growth. D-mannitol, L-rhamnose, salicin and sucrose do not support growth. Table 2 below compares the carbon utilization patterns observed for A10255.1 and *S. gardneri* ATCC 23911.

TABLE 2

| Utilization of Carbon Compounds by A10255.1 and *S. gardneri* ATCC 23911 | | |
|---|---|---|
| Carbon Source | A10255.1 | *S. gardneri* |
| No carbon | $-^a$ | $-$ |
| L-arabinose | $+^b$ | $+$ |
| D-fructose | $+$ | $+$ |
| D-galactose | $+$ | $+$ |
| D-glucose | $+$ | $+$ |
| i-inositol | $+$ | $-$ |
| D-mannitol | $-$ | $-$ |
| raffinose | $+$ | $+$ |
| L-rhamnose | $-$ | $+$ |
| salicin | $-$ | $-$ |
| sucrose | $-$ | $+$ |
| D-xylose | $+$ | $+$ |

$-^a$ = no utilization
$+^b$ = utilization

Culture A10255.1 hydrolyzed starch and, partially hydrolyzed skim milk, produced catalase, liquified gelatin, and reduced nitrates to nitrites.

A10255.1 will tolerate up to 6 percent sodium chloride and will grow at temperatures ranging from 4° C. to 40° C.

Melanoid pigments are produced when A10255.1 is grown in tryptone-yeast extract broth (ISP No. 1) and on slants of peptone-yeast extract iron agar (ISP No. 6). No melanoid pigments were produced on slants of tyrosine agar (ISP No. 7).

Species Determination

Using the cultural, morphological, and physiological characteristics of A10255.1, comparison was made with the published descriptions of similar species. Four species of Streptomyces were selected to examine in simultaneous laboratory comparison:

*Streptomyces aureofasciculus*[a]
*Streptomyces aureomonopodiales*[a]
*Streptomyces flavochromogenes*[b]
*Streptomyces gardneri*[c]

[a]E. B Shirling and D. Gottlieb, "Cooperative Description of Type Cultures of *Streptomyces*", *Int. J. Syst. Bacteriol.*, 19(4), 375–390 (1969).

[b]E. B. Shirling and D. Gottlieb, "Cooperative Description of Type Cultures of *Streptomyces*", *Int. J. Syst. Bacteriol.*, 22(4), 265–394 (1972).

[c]E. B. Shirling and D. Gottlieb, "Cooperative Description of Type Cultures of *Streptomyces*", *Int. J. Syst. Bacteriol.*, 18(4), 279–392 (1968).

Laboratory companions indicated significant differences with *S. aureofasciculus* and *S. flavochromo genes*, and good agreement with *S. aureomonopodiales* and *S. gardneri*. However, since *S. aureomonopodiales* is not in the Approved List of Bacterial Names, it was removed from consideration.

A10255.1 is quite similar to *S. gardneri* in cultural, morphological, and physiological characteristics. The predominant cultural feature that distinguishes both strains is the very poor formation of aerial hyphae on most media. *S. gardneri* is described in the literature as belonging in the Gray (GY) series. However, in the original description by Waksman [S. A. Waksman, supra.], and in.laboratory comparisons with A10255.1, it produced white (W) and gray (GY) aerial hyphae. The reverse color of both cultures is almost identical. Both cultures possess a Rectus-flexibilus (RF) morphology, smooth spore surface ornamentation, cylindrical spore shape, and chains of 10–50 spores.

Catalase production, liquefaction of gelatin, melanoid pigment production, reduction of nitrate, and hydrolysis of milk and starch were the same for both strains.

Differences between A10255.1 and *S. gardneri* are minimal. *S. gardneri* had less tolerance to sodium chloride and a lower temperature range than A10255.1. The utilization of L-rhamnose, sucrose, and inability to utilize i-inositol distinguish *S. gardneri* from A10255.1. These similarities and differences are summarized below.

| Comparison Between A10255.1 and *Streptomyces gardneri* | |
|---|---|
| Similarities | Differences |
| Aerial spore mass color (W) | Carbon utilization |
| Catalase positive | Sodium chloride tolerance |
| Cell wall hydrolysates (LL-DAP) | Temperature range |

-continued

| Comparison Between A10255.1 and *Streptomyces gardneri* | |
|---|---|
| Similarities | Differences |
| Distinctive pigments absent | |
| Gelatin liquefaction | |
| Morphology (RF) | |
| Nitrate reduction | |
| Partial milk hydrolysis | |
| Reverse pigmentation | |
| Soluble pigments absent | |
| Spore chain length | |
| Spore shape | |
| Spore surface ornamentation (Sm) | |
| Starch hydrolysis | |

The similarities and differences between the two cultures are set forth below in detail in Table 3:

TABLE 3

| Comparison of A10255.1 and *S. gardneri* ATCC 23911 | | |
|---|---|---|
| Characteristics | A10255.1 | *S. gardneri* |
| Aerial spore mass color | (W) | (W) |
| Carbon utilization pattern | | |
| i-inositol | + | − |
| L-rhamnose | − | + |
| sucrose | − | + |
| Catalase | + | + |
| Cell wall type | I | I |
| Distinctive pigments | − | − |
| Gelatin liquefaction | + | + |
| Melanoid pigment production | | |
| ISP No. 1 | + | + |
| ISP No. 6 | + | + |
| ISP No. 7 | − | − |
| Morphology | (RF) | (RF) |
| NaCl tolerance - % | 6 | 4 |
| Nitrate reduction | + | + |
| Reverse color | YBr | YBr |
| Skim milk hydrolysis | partial | partial |
| Soluble pigments | − | − |
| Spore chain length | 10–50 | 10–50 |
| Spore shape | cylindrical | cylindrical |
| Spore surface | smooth | smooth |
| Starch hydrolysis | + | + |

TABLE 3-continued

| Comparison of A10255.1 and *S. gardneri* ATCC 23911 | | |
|---|---|---|
| Characteristics | A10255.1 | *S. gardneri* |
| Temperature range - °C. | 4–40 | 4–37 |

The results of the above comparisons indicate that A10255.1 is very similar to *S. gardneri*. Therefore culture A10255.1 is classified as a strain of *Streptomyces gardneri* (Waksman, 1942) Waksman 1961,- ATCC 23911. *S. gardneri* is recognized in the Approved List of Bacterial Names [V. B. D. Skerman et al., "Approved Lists of Bacterial Names", *International J. Syst. Bacteriol.*, 30(1), 225–420 (1980) and consequently is a validly published species.

It should be mentioned that Kurylowicz et al. [W. Kurylowicz, A. Paszkiewicz, W. Woznicka, and W. Kurzatkowski, "Numerical Taxonomy of Streptomyces", Polish Medical Publishers, 1975], when classifying Streptomyces, in both the Wroclaw dentrite of similarity and the Overall Similarity Method numerical methods place *S. aureomonopodiales* and *S. gardneri* in the same cluster. A dendrogram based on this study relates these two strains at a percentage similarity of 94. This similarity suggests that a distinction in species is not justified.

The *Streptomyces gardneri* culture described above has been deposited and made a part of the stock culture collection of the Northern Regional Research Division, U.S. Department of Agriculture, Agricultural Research Service, Peoria, IL, 61604. Upon issuance of the instant specifications, the culture will be made available to the public from this branch of the Department of Agriculture under the number NRRL 15537.

Taxonomy of the A10255.2 strain

Significant similarities, in addition to all the differences between the A10255.1 strain and the instant A10255.2 strains, are set forth below in Tables 4 and 5.

TABLE 4

| | | Cultural Characteristics of A10255.1 and A10255.2 | |
|---|---|---|---|
| Agar | | A10255.1 | A10255.2 |
| ISP No. 2 | [a]G: | Fair | Fair |
| | [b]R: | 72.d.OY | 72.d.OY |
| | [c]Am: | Poor: b White (edges only) d light Gray | Poor: b White to 2 ba Pale yellow |
| | Sp: | None | None |
| ISP No. 3 | G: | Trace to Fair | Trace to Fair |
| | R: | 70.1.OY | 93.y.Gray |
| | Am: | Trace: b White (edges only) | Trace: b White |
| | Sp: | None | None |
| Calcium Malate | G: | Fair (malate not hydrolyzed) | Fair (malate not hydrolyzed) |
| | R: | 79.1.gy.yBr | 79.1.gy.yBr |
| | Am: | None | None |
| | SP: | None | None |
| Czapek's | G: | Fair | None |
| | R: | 93.yGray | |
| | Am: | Poor: b White | |
| | Sp: | None | |
| Glucose Asparagine | G: | Fair | Poor |
| | R: | 72.d.OY | 90.gy.Y |
| | Am: | Poor: (edges only) b White | None |
| | Sp: | None | None |
| ISP No. 7 | G: | Good | Good |
| | R: | 54.brO | 54.brO |
| | Am: | Poor: b White | Fair: b White |
| | Sp: | Light brown | Light brown |
| Glycerol | G: | Fair | Abundant |

TABLE 4-continued

Cultural Characteristics of A10255.1 and A10255.2

| Agar | | A10255.1 | A10255.2 |
|---|---|---|---|
| Glycine | R: | 53.m.O (no pH change) | 50.s.O |
| | Am: | None | Good: 5 cb gy.yPk. |
| | Sp: | Light-orange | Light-orange |
| TPO | G: | Good | Abundant |
| | R: | 54. brO (no pH change) | 51.deep O |
| | Am: | Poor: (edges only) 3ca pale orange yellow | Good: 2 ba Pale yellow |
| | Sp: | light orange-brown | light orange-brown |
| ISP No. 4 | G: | Fair | Fair |
| | R: | 71.m.OY | 77.m.yBr. |
| | Am: | Poor: b White (edges only) | Fair: b White to 2 ba Pale yellow |
| | Sp: | None | None |
| ISP No. 5 | G: | Fair | Good |
| | R: | 70.1.OY | 70.1.OY |
| | Am: | Fair: b White to d l.Gray | Good: b White to 2 ba Pale yellow |
| | Sp: | None | None |

<sup>a</sup>G = Growth; R = Reverse; Am = Aerial Mycelia; Sp = Soluble pigment.
<sup>b</sup>Coding of reverse colors follows the ICSS-NBS System, Supra.
<sup>c</sup>Coding of aerial color follows the Color Harmony Manual, Supra.

TABLE 5

Comparison of A10255.1 and A10255.2 Strains

| Characteristic | A10255.1 | A10255.2 |
|---|---|---|
| Aerial spore mass color | W to GY | W to Y |
| Carbon utilization pattern | identical | |
| Catalase | + | + |
| Cultural characteristics: | | |
| aerial hyphae on glycerol-glycine agar | − | + |
| growth on Czapek's agar | + | − |
| Distinctive pigments on certain media | + | + |
| Gelatin liquefaction | + | + |
| Melanoid pigment production | + | + |
| Morphology | RF | RF |
| NaCl tolerance % | 6 | 6 |
| Nitrate reduction | + | + |
| Reverse color | Ybr | Ybr |
| Skim milk hydrolysis | Partial | Complete |
| Soluble pigments on certain media | + | + |
| Spore chain length | 10–50 | 10–50 |
| Spore shape | Cylindrical | Cylindrical |
| Spore size - μM | 1.0 × 0.6 | 1.3 × 0.6 |
| Spore surface | Smooth | Smooth |
| Starch hydrolysis | + | + |
| Temperature range - °C. | 4–40 | 4–37 |

The *Streptomyces gardneri* culture A10255.2 described above has been deposited and made a part of the stock culture collection of the Northern Regional Research Division, U.S. Department of Agriculture, Agricultural Research Service, Peoria, Ill., 61604. Upon issuance of the instant specification, the culture will be made available to the public from this branch of the Department of Agriculture under the number NRRL 15922.

Production of the Compounds and their Biological Activity

The A10255 antibiotic complex is produced by culturing the previously undescribed microorganism Streptomyces gardneri, NRRL 15922, or an A10255-producing mutant, variant, or recombinant thereof, in a culture medium containing assimilable sources of carbon, nitrogen, and inorganic salts, under submerged aerobic fermentation conditions until the A10255 antibiotic complex is produced, and preferably until a substantial level of antibiotic activity is produced. Most of the antibiotic activity is generally found associated with the mycelia, while minor amounts of antibiotic activity are found in the broth. The A10255 complex is most readily separated from the fermentation mixture by removal of the mycelia (the biomass), by filtration. The broth is generally discarded. The antibiotic complex is then isolated from the mycelia.

The mycelia are extracted with polar solvents (such as 4:1 acetone:water), concentrated, acidified, again extracted with an organic solvent (ethyl acetate, for example), and the resultant solutions are concentrated to precipitate the A10255 complex.

Alternatively, the mycelia are extracted with polar solvents (such as 4:1 acetone:water). The combined extracts are concentrated in vacuo to an aqueous suspension. The crude antibiotic is isolated by filtration or centrifugation, and further dried in vacuo.

The A10255 complex can be used without further purification and mixed directly into animal feed or animal feed premix. Alternatively, the A10255 antibiotic complex can be further purified and separated into its individual factors by well-known chromatographic techniques such as thin layer chromatography, column chromatography, and especially various high performance liquid chromatography procedures. Some specific procedures for isolating the individual factors are discussed in the Experimental Section.

A number of different media may be used with NRRL 15922 to produce the A10255 complex. For economy in production, optimal yield, and ease of product isolation, however, certain culture media are preferred. These media should contain assimilable sources of carbon, nitrogen, and inorganic salts. Suitable carbon sources include glucose, starch, maltose, fructose, and glycerol. Optimum levels of carbon sources are from about 2 to about 5 percent by weight.

Preferred nitrogen sources include soybean grits, acid digest of soybeans, cottonseed meal, peanut meal, fish meal, acid or enzymatic digests of casein, ammonium salts, nitrate salts, glycine, alanine, serine, asparagine, and glutamine.

Essential trace elements necessary for the growth and development of the organism may occur as impurities in other constituents of the media in amounts sufficient to meet the growth and biosynthetic requirements of the organism. However, it may be beneficial to incorporate in the culture media additional soluble nutrient inorganic salts capable of yielding sodium, potassium, magnesium, calcium, ammonium, chloride, carbonate, phosphate, sulfate, nitrate, and like ions.

Although small quantities of the A10255 antibiotic may be obtained by shake-flask culture, submerged aerobic fermentation in tanks is a preferred method for producing substantial quantities of the A10255 antibiotic. For tank fermentation, it is preferable to use a vegetative inoculum. The vegetative inoculum is prepared by inoculating a small volume of culture medium with the spore form, or mycelial fragments, to obtain a fresh, actively growing culture of the organism. The vegetative inoculum is then transferred to a tank where, after a suitable incubation time, the A10255 antibiotic is produced in optimal yield.

The A10255.2 strain produces the A10255 complex over a temperature range of from about 25 to about 37° C. Optimum production of the A10255 antibiotic complex appears to occur at a temperature of about 30° to about 32° C.

As is customary in aerobic submerged culture processes, sterile air is dispersed through the culture medium. For efficient growth of the organism, the volume of air used in tank production is in the range of from about 0.25 to about 1.0 volumes of air per volume of culture medium per minute (v/v/m), with from about 150 to about 400 RPM agitation. An optimum initial rate in a 165-liter vessel containing 115 liters of fermentation medium is about 0.5 v/v/m, with agitation provided by conventional impellers rotating initially at about 300 RPM.

The fermentation of the A10255.2 strain generally produces antibiotic activity after about 20 hours. Peak antibiotic production occurs at from about 90 hours to about 140 hours fermentation time.

Production of the A10255 antibiotic can be monitored during the fermentation by either agar diffusion using *Bacillus subtilis* ATCC 6633, or by a turbidimetric method using *Staphylococcus aureus* ATCC 9114.

The A10255 complex and individual factors are antimicrobial agents and are especially active against gram-positive microorganisms, as illustrated by the following in vitro and in vivo test data. In the following Table 6 is presented the minimum inhibitory concentration, (MIC, in micrograms/milliliter) for the factors against a sampling of pathogenic gram-positive and gram-negative bacteria. The MIC values were obtained by the standard agar dilution method test.

TABLE 6

Activity of A10255 Compounds vs. Pathogenic Microorganisms

| Test Organism | MIC (mcg/ml) | | | |
|---|---|---|---|---|
| | B | C | E | F |
| *Staphylococcus aureus* X1.1 | 0.125 | 0.03 | 0.25 | 0.03 |
| *Staphylococcus aureus* V41 | 0.5 | 0.125 | 0.25 | 0.06 |
| *Staphylococcus aureus* X400 | 0.5 | 0.125 | 0.5 | 0.06 |
| *Staphylococcus aureus* S13E | 0.5 | 0.06 | 0.125 | 0.03 |
| *Staphylococcus epidermidis* 270 | 0.25 | 0.03 | 0.25 | 0.03 |
| *Staphylococcus epidermidis* 222 | 0.5 | 0.125 | 0.5 | 0.06 |
| *Streptococcus pyogenes* C203 | 0.125 | 0.06 | 0.125 | 0.03 |
| *Streptococcus pneumoniae* Park I | 0.125 | 0.015 | 0.125 | 0.015 |
| *Streptococcus group* D X66 | 0.25 | 0.06 | 0.25 | 0.06 |
| *Streptococcus group* D 2041 | 0.5 | 0.125 | 0.25 | 0.125 |
| *Hemophilus influenzae* C.L. (sens.) | >128 | 64 | >128 | >128 |
| *Hemophilus influenzae* 76 (res.) | >128 | 16 | 16 | 128 |

The A10255 compounds also demonstrate excellent antimicrobial activity against a number of *Clostridium difficile* strains. In particular, in standard agar dilution tests the A10255 complex and factors B, C, E, and F exhibited MIC's of less than or equal to 0.03 microgram/milliliter. By comparison, in the same tests for the complex and factors B and C, the antibiotic vancomycin exhibited an MIC of 2 or 4 micrograms/milliliter.

The A10255 complex and factor C were tested against several Bacteroides species and demonstrated excellent antimicrobial activities. The results of this agar-dilution test are set forth below in Table 7.

TABLE 7

Activity of A10255 Compounds vs. Select Bacteroides Species Strains

| Test Organism | MIC (mcg/ml) | |
|---|---|---|
| | A10255 Complex | Factor C |
| *B. Fragilis* strains | | |
| 1877 | 0.5 | 0.5 |
| 103 | 0.5 | 0.5 |
| 104 | 0.06 | 0.06 |
| 106 | 0.06 | 0.06 |
| 107 | 1.0 | 1.0 |
| 108 | 1.0 | 1.0 |
| 110 | 0.5 | 0.5 |
| 111 | 1.0 | 1.0 |
| 112 | 1.0 | 1.0 |
| 113 | 1.0 | 1.0 |
| 1451 | 0.25 | 0.25 |
| 1470 | 1.0 | 1.0 |
| 2 | 0.5 | 0.5 |
| 9 | 1.0 | 1.0 |
| 9032 | 1.0 | 1.0 |
| *B. corrodens* 1874 | 0.5 | 0.5 |
| *B. vulgatis* 1563 | 0.25 | 0.25 |
| *B. thetaiotaomicxon* 1438 | 0.5 | 0.5 |
| *B. thetaiotaomicxon* 1900A | 0.5 | 0.5 |

The A10255 complex and the individual factors have demonstrated antimicrobial activity against a wide variety of anaerobic microorganisms. The antimicrobial activity is set forth below in Table 8. The results set forth in the Table are MIC values from a standard agar dilution test.

TABLE 8

Activity of A10255 Compounds vs. Anaerobic Bacteria

| Test Organism | MIC (mcg/ml) | | | | |
|---|---|---|---|---|---|
| | Complex | B | C | E | F |
| *Clostridium difficile* 2994 | 0.125 | ≦0.06 | 0.125 | ≦0.03 | ≦0.03 |
| *Clostridium perfringens* 81 | ≦0.06 | ≦0.06 | ≦0.06 | ≦0.03 | ≦0.03 |

TABLE 8-continued

Activity of A10255 Compounds vs. Anaerobic Bacteria

| Test Organism | MIC (mcg/ml) Complex | B | C | E | F |
|---|---|---|---|---|---|
| *Clostridium septicum* 1128 | ≦0.06 | ≦0.06 | ≦0.06 | ≦0.03 | ≦0.03 |
| *Eubacterium aerofaciens* 1235 | ≦0.06 | ≦0.06 | ≦0.06 | ≦0.03 | ≦0.03 |
| *Peptococcus asaccharolyticus* 1302 | 1.0 | ≦0.06 | 1.0 | ≦0.03 | 0.06 |
| *Peptococcus prevoti* 1281 | ≦0.06 | ≦0.06 | ≦0.06 | 0.125 | 0.125 |
| *Peptostreptococcus anaerobius* 1428 | ≦0.06 | 2 | ≦0.06 | 2 | 1.0 |
| *Peptococcus intermedius* 1264 | 1.0 | >32 | 1.0 | 0.5 | 0.25 |
| *Propionibacterium acnes* 79 | 0.125 | >32 | 0.125 | 0.5 | 0.125 |
| *Bacteroides fragilis* 111 | 1.0 | >32 | 1.0 | 4 | 1.0 |
| *Bacteroides fragilis* 1877 | 2 | >32 | 2 | 4 | 1.0 |
| *Bacteroides fragilis* 1936B | 0.5 | >32 | 0.5 | 4 | 1.0 |
| *Bacteroides thetaiotaomicron* 1438 | 0.5 | 0.5 | 0.5 | 1.0 | 0.25 |
| *Bacteroides melanionogenicus* 1856/28 | 1.0 | >32 | 1.0 | 4 | 4 |
| *Bacteroides melaninogenicus* 2736 | 0.5 | 4 | 0.5 | 0.5 | 0.125 |
| *Bacteroides vulgatis* 1211 | 0.5 | 4 | 0.5 | 1.0 | 0.25 |
| *Bacteroides corrodens* 1874 | 0.25 | >32 | 0.25 | 2 | 0.5 |
| *Fusobacterium symbiosum* 1470 | ≦0.06 | ≦0.06 | <0.06 | ≦0.03 | ≦0.03 |
| *Fusobacterium necrophorum* 6054A | ≦0.06 | ≦0.06 | <0.06 | ≦0.03 | ≦0.03 |

The A10255 complex and factor B demonstrated an LD$_{50}$ of greater than 300 mg/kg×1 and greater than 75 mg/kg×1, respectively. The results were obtained by intraperitoneal injection in mice.

The antimicrobial compounds (i.e., A10255 complex and individual factors) made by the process of this invention are useful for the therapeutic or prophylactic treatment of infections in warm-blooded animals caused by pathogenic bacteria. The antimicrobial compounds can be administered orally, parenterally (for example, intravenously, intramuscularly or subcutaneously) or as a topical ointment or solution in treating bacterial infections of warm-blooded animals.

The pharmaceutical compositions of the A10255 complex or the individual factors thereof are composed of a therapeutically active amount of the instant antibiotic compounds (i.e., the A10255 complex or factor B, factor C, factor E or factor F separately) and a suitable vehicle. With regard to compositions for oral administration (for example tablets and capsules), the term "suitable vehicle" means common excipients such as binding agents, for example, syrup, acacia, gelatin, sorbitol, tragacanth, polyvinylpyrrolidine (Povidone), methylcellulose, ethylcellulose, sodium carboxymethylcellulose, hydroxypropylmethylcellulose, sucrose, and starch; fillers and carriers, for example corn starch, gelatin, lactose, sucrose, microcrystalline cellulose, kaolin, mannitol, dicalcium phosphate, sodium chloride, and aliginic acid, disintegrators such as croscarmellose sodium, microcrystalline cellulose, corn starch, sodium starch glycolate, aliginic acid, and mutable wetting agents such as sodium lauryl sulfate; and lubricants such as magnesium stearate and other metallic stearates, stearic acid, silicone fluid, talc, waxes, oils, and colloidal silica. Flavoring agents such as peppermint, oil of wintergreen, cherry flavoring or the like can also be used. It may be desirable to add a coloring agent to make the dosage form more appealing visually or to help identify the product. The tablets may also be coated by methods well known in the art.

The pharmaceutical compositions may also be in the form of oral liquid preparations, which may be either a) aqueous or oily suspensions, solutions, emulsions or syrups; or b) a dry powder to be reconstituted with water or another suitable vehicle before use. When used in conjunction with such oral liquid preparations, the term "suitable vehicle" means conventional additives such as suspending agents, for example, sorbitol, syrup, methyl cellulose, glucose/sugar syrup, gelatin, hydroxyethylcellulose, carboxymethyl cellulose, or aluminum stearate gel; or hydrogenated edible oils, for example, almond oil, fractionated coconut oil, oily esters, propylene glycol or ethyl alcohol; and preservatives such as methyl or propyl p-hyroxybenzoates or sorbic acid.

The pharmaceutical composition can also be for intravenous (IV) use. Specifically, a water soluble form of the antibiotic compound can be dissolved in one of the commonly used intravenous fluids and administered by infusion. When used in conjunction with compositions for IV use, the term "suitable vehicle" means such fluids as physiological saline, Ringer's solution or 5% dextrose solution For intramuscular preparations a sterile formulation of a suitable salt form of the antibiotic compound (for example, the hydrochloride salt or sodium salt) can be formulated with a "suitable vehicle". Examples of such sterile formulations are a suitable salt form either dissolved in a pharmaceutical diluent (for example, Water-for-Injection, physiological saline, 5% glucose) or suspended in an aqueous base or a pharmaceutically acceptable oil base (for example, an ester of a long chain fatty acid such as ethyl oleate).

Topical compositions can be formulated with "suitable vehicles" such as hydrophobic or hydrophilic bases. Such bases include ointments, creams or lotions.

Veterinary pharmaceutical compositions of the antibiotic compounds may be administered in the feed or the drinking water of farm animals. Alternatively, the compounds can be formulated as intramammary preparations with "suitable vehicles" such as long- or quick-release bases.

The antibiotic compounds made by the process of the instant invention can also be formulated in unit dosage form in sterile vials, sterile plastic pouches containing a part with a septum, or sterile, hermetically sealed ampoules. The anitibiotic compound (or the corresponding pharmaceutically-acceptable salt) may be a dry powder or in crystalline or lyophilized form. The amount of the antibiotic compound per unit dosage may vary from about 250 milligrams to about 10 grams.

A "therapeutically effective amount" of the A10255 antibiotic compounds is from approximately 3.5 mg to about 50 mg of compound per kilogram of body weight. This amount generally totals from about 1 gram to about 27 grams per day for an adult human.

A method for treating or controlling infectious diseases caused by gram-positive and gram-negative organisms in warm-blooded animals comprises administering to the animal a therapeutically effective amount of the A10255 antibiotic compounds. A typical daily dose for an adult human in this method is from about 1 gram to about 12 grams.

In practicing this method, the antibiotic compound can be administered in a single daily dose or in multiple doses per day. The treatment regime may require administration over extended periods of time, for example, for several days or for from two to three weeks. The amount administered per dose or the total amount administered will depend on such factors as the nature and severity of the infection, the age and general health of the patient, and the tolerance to the antibiotic compound of both the patient and the microorganism or microorganisms involved in the infection.

The following Examples are provided to further illustrate the invention. It is not intended that the invention be limited in scope by reason of any of the following Examples.

EXPERIMENTAL SECTION

Example 1

The following medium was prepared for use in the agar slant culture of the A10255.2 producing microorganism:

| Production of A10255 Complex | |
|---|---|
| Ingredient | Amount (g/L) |
| Pre-cooked oatmeal | 60.0 |
| Yeast | 2.5 |
| $K_2HPO_4$ | 1.0 |
| KCl | 0.5 |
| $MgSO_4.7H_2O$ | 0.5 |
| $FeSO_4.7H_2O$ | 0.1 |
| Deionized water q.s. to | 1 liter |

The pH of the resultant medium was adjusted to pH 7.3 with aqueous sodium hydroxide. The medium was then autoclaved, yielding a sterilized medium with a pH of 6.7.

Spores of S. gardneri, NRRL 15922, were inoculated on a nutrient agar slant composed of the above sterilized medium. The inoculated slant was incubated for 7-10 days at a temperature of 30° C. The mature slant culture was then covered with calf serum and scraped with a sterile tool to loosen the spores and mycelia. The resultant suspension was transferred to small tubes and lyophilized for preservation. One lyophilized pellet was used to inoculate sterile vegetative culture medium (50 ml, contained in a 250 ml widemouth Erlenmeyer Flask) of the following composition:

| Ingredient | Amount (g/L) |
|---|---|
| Glucose | 15.0 |

-continued

| Ingredient | Amount (g/L) |
|---|---|
| Dextrin | 20.0 |
| Soybean grits | 10.0 |
| Corn steep liquor | 10.0 |
| Yeast extract | 1.0 |
| $CaCO_3$ | 2.0 |
| Tap water q.s. to | 1 liter |

The pH of the medium was adjusted to 6.7 with aqueous sodium hydroxide. The medium was autoclaved, which raised the pH of the medium to between 6.8 and 7.0.

The inoculated vegetative medium was incubated for 48 hours at 30° C. on a shaker rotating through an arc two inches in diameter at 250 RPM. The resulting vegetative medium culture was used either to inoculate small fermentors (the inoculum being approximately 1% per volume of fermentors medium), or to inoculate second stage flasks for the production of a larger volume of inoculum.

Bump Medium

Two wide-mouth Erlenmeyer flasks (2 liter capacity) were charged with amedium (400 ml each) having the following composition:

| Ingredient | Amount (g/L) |
|---|---|
| Glucose | 15.0 |
| Dextrin | 20.0 |
| Soybean grits | 15.0 |
| Corn steep liquor | 10.0 |
| Yeast extract | 1.0 |
| $CaCO_3$ | 5.0 |
| Tap water q.s. to | 1 liter |

The medium in each Erlenmeyer flask was inoculated with 2.5% of its volume of the above vegetative culture. The inoculated medium was incubated at 30° C. for 23 hours on a rotary shaker at 250 RPM to yield a "bump" culture.

Large Scale Fermentation

The above "bump" culture (800 ml) was used to inoculate the following medium (115 liters):

| Ingredient | Amount (g/L) |
|---|---|
| Antifoam* | 0.200 |
| Propylene glycol (MW2000) | 2.000 ml |
| Glucose | 1.000 |
| Casein | 16.000 |
| $NaH_2PO_4.H_2O$ | 0.100 |
| Blackstrap molasses | 40.000 |
| $CaCO_3$ | 5.000 |
| Tap water q.s. to | 110 liters |

*Sag 471, Silicone Antifoaming Agent, Dow Corning Co.

The medium was contained in a 165 liter fermentor. The pH of the medium was adjusted to 6.9 with 5N aqueous sodium hydroxide. The mixture was sterilized for 45 min. at 17-19 psi at 121° C. After the sterilization procedure the medium had pH 6.8. The sterilized medium was aerated with sterile air at the rate of 0.5 v/v/m, stirred with conventional agitators at an initial rate of 300 RPM, and allowed to ferment for about 7 days at a temperature of 30° C. During the fermentation period, the pH was maintained at 7.0, dissolved oxygen level was maintained at 45% of air saturation and glucose was fed to the medium at a constant rate of 3.5–4.0 g/l/day. After 24 hours, Hy Case Amino (Acid hydrosylate of casein, Humko Sheffield Chemical Co., Lyndhurst, New Jersey) was also fed into the medium at a constant rate of 3 g/l day.

The crude A10255 complex was isolated in a procedure similar to that of Example 3 below.

Example 2

Large Volume Fermentation of the A10255.2 Strain

Vegetative Inoculum

As a starting point for large volume fermentations of the A10255.2 strain (i.e., larger volumes than Example 1 above), vegetative innoculum is prepared in two stages. Both stages use the following medium:

| Ingredients | Amount |
| --- | --- |
| Glucose | 1.5% |
| Soybean Grits | 1.5% |
| Potato Dextrin | 2.0% |
| Corn Steep Liquor | 1.0% |
| Yeast Extract | 0.1% |
| Calcium Carbonate | 0.2% |
| Tap water | to volume |

The first stage of incubation was carried out in a 250 ml flask containing 80 ml of the sterilized medium. The flask was inoculated with a lyophilized pellet of the A10255.2 culture. The medium was incubated at 30° C. for 48 hours on a rotary shaker at 250 rpm.

A portion (10 ml) of the first stage inoculum was used to inoculate a sterilized second stage incubation medium, composed of 400 ml of the above medium contained in a two liter wide-mouth Erlenmeyer flask. This second stage medium was incubated at 30° C. for 24 hours on a rotary shaker at 250 rpm. The incubated medium was used below in the tank fermentation.

Tank Fermentation

The medium from the above Second Stage Vegetative Inoculum was used to inoculate the following tank medium contained in a 150 liter fermenter:

| Ingredients | Amount |
| --- | --- |
| Cerelose | 1.5% |
| Potato Dextrin | 2.0% |
| Corn Steep Liquor | 1.0% |
| Soybean Grits | 1.5% |
| Calcium Carbonate | 0.5% |
| SAG 471* | 0.01% |
| Tap water | to 120 liters |

*Silicone Antifoaming Agent, Dow Corning Co.

This medium was first sterilized by autoclaving. After sterilization, the pH of the medium was adjusted to 6.5 by the addition of 5N sodium hydroxide solution. The medium was then inoculated and fermented at 30° C. for about 24 hours. During fermentation the medium was aerated with sterile air at an initial rate of 1 cubic foot per minute (cfm) and agitated by a conventional stirrer at an initial rate of 350 rpm.

Large Scale Fermentation

A portion of the above tank medium (40 liters) was used to inoculate the following large-scale medium:

| Ingredients | Amount |
| --- | --- |
| Antifoam* | 0.02% |
| Propylene glycol (mw 2000) | 0.02% |
| Molasses | 4.00% |
| Calcium Carbonate | 0.50% |
| Acid hydrosylate of casein** | 1.60% |
| NaH$_2$PO$_4$.H$_2$O | 0.01% |
| Glucose | 0.10% |
| Tap water | to 1200 gallons |

*SAG 471 silicone defoaming agent
**Hy Case, Humko Sheffield Chemical Co., Lyndhurst, New Jersey The medium was contained in a 1600 gallon fermenter. The pH of the medium was adjusted to 7.0 by the addition of 5N sodium hydroxide solution. The medium was sterilized for thirty minutes at 121° C. at 17 psi. The sterilized medium was aerated with sterile air at an initial rate of 20 cubic feet per minute, stirred with a conventional agitator at an initial speed of 100 rpm, and allowed to ferment for about 6 days at 30° C. During the fermentation period, the pH of the medium was maintained at about 7.0, the dissolved oxygen content of the medium was maintained at about 45% of air saturation, and glucose was fed to the medium at a constant rate of 4 g/l day. After 24 hours, Hy Case was also fed to the medium at the rate of 3 g/l day.

Example 3

Isolation of the A10255 Antibiotic Complex

Whole fermentation broth (5000 l) of the A10255.2 organism was harvested and filtered using filter aid (Hyflo Super-Cel, Johns Manville Products Corp.). The filtrate and water wash (1200 l of water) of the biomass were discarded.

The biomass was then extracted batchwise with a mixture of 1:4 water:acetone (2000 l). The extraction was repeated and the extracts were combined (total: 4000 liters). The combined extracts contained the bulk of the A10255 complex.

The combined extracts were concentrated under vacuum to an aqueous suspension. Upon standing, a fine solid precipitated from the suspension. The solid was the crude A10255 complex. The concentrated extracts were then centrifuged and the supernatant discarded.

The solids obtained from the centrifugation were dried in vacuo to give 1.5 Kg of a brown powder containing 423 microgram/milligram of A10255 antibiotic activity.

Example 4

Separation of the Factors from the A10255 Complex

The separation of the individual antibiotic factors (B, C, E, and F) was obtained following in general the procedures described in the co-filed U.S. patent application No. 05/941,894 of Karl H. Michel, LaVerne D. Boeck, Herbert A. Kirst, Eugene T. Seno and Marvin M. Hoehn, herein incorporated by reference.

We claim:

1. A process for producing the A10255 complex, which comprises cultivating *Streptomyces gardneri* NRRL 15922, or an A10255-producing variant, for mutant thereof, in a culture medium containing assimilable sources of carbon, nitrogen, and inorganic salts under submerged aerobic fermentation conditions until the A10255 antibiotic complex is produced.

2. The process of claim 1, which includes the additional step of separating the A10255 complex from the culture medium.

3. The process of claim 2, which includes the additional step of isolating antibiotic A10255 factor B from the separated A10255 complex.

4. The process of claim 2, which includes the additional step of isolating antibiotic A10255 factor C from the separated A10255 complex.

5. The process of claim 2, which includes the additional step of isolating antibiotic factor E from the separated A10255 complex.

6. The process of claim 2, which includes the additional step of isolating antibiotic A10255 factor F from the separated A10255 complex.

7. A biologically pure culture of the microorganism *Streptomyces gardneri* NRRL 15922, or a mutant, or variant thereof, which produces a recoverable amount of the antibiotic A10255 complex.

8. A biologically pure culture of the microorganism *Streptomyces gardneri* NRRL 15922 of claim 7.

* * * * *

UNITED STATES PATENT AND TRADEMARK OFFICE
CERTIFICATE OF CORRECTION

PATENT NO.    : 5,286,631

DATED         : February 15, 1994

INVENTOR(S)   : LaVerne D. Boeck, et al.

It is certified that an error appears in the above-identified patent and that said Letters Patent is hereby corrected as shown below:

```
Column 20, Line 64 "...NRRL 15922, or an A10255-producing variant, for..."
should read --...NRRL 15922, an A10255-producing variant, or...--
```

Signed and Sealed this

Thirtieth Day of August, 1994

BRUCE LEHMAN

*Attest:*

*Attesting Officer*     *Commissioner of Patents and Trademarks*